United States Patent
Malek

(10) Patent No.: US 7,255,713 B2
(45) Date of Patent: Aug. 14, 2007

(54) SYSTEMS AND METHODS FOR AGENT DELIVERY

(76) Inventor: Michel H. Malek, 577 W. Hawthorne Pl., Chicago, IL (US) 60657

( * ) Notice: Subject to any disclaimer, the term of this patent is extended or adjusted under 35 U.S.C. 154(b) by 0 days.

(21) Appl. No.: 10/739,932

(22) Filed: Dec. 18, 2003

(65) Prior Publication Data

US 2005/0137707 A1 Jun. 23, 2005

(51) Int. Cl.
 *A61F 2/44* (2006.01)
 *A61B 17/86* (2006.01)
(52) U.S. Cl. .................... 623/17.12; 606/73
(58) Field of Classification Search ............ 623/17.12, 623/17; 606/73
 See application file for complete search history.

(56) References Cited

U.S. PATENT DOCUMENTS

| | | | |
|---|---|---|---|
| 4,653,489 A | | 3/1987 | Tronzo |
| 4,760,844 A | | 8/1988 | Kyle |
| 4,772,287 A | * | 9/1988 | Ray et al. ................. 623/17.12 |
| 4,932,975 A | | 6/1990 | Main et al. |
| 5,047,030 A | | 9/1991 | Draenert |
| 5,147,404 A | | 9/1992 | Downey |
| 5,306,310 A | | 4/1994 | Siebels |
| 5,618,286 A | | 4/1997 | Brinker |
| 5,681,289 A | | 10/1997 | Wilcox et al. |
| 5,800,407 A | | 9/1998 | Eldor |
| 5,871,484 A | | 2/1999 | Spievack et al. |
| 5,989,290 A | | 11/1999 | Biedermann et al. |
| 6,001,130 A | | 12/1999 | Bryan et al. |
| 6,077,265 A | | 6/2000 | Werding et al. |
| 6,210,376 B1 | | 4/2001 | Grayson |
| 6,214,012 B1 | | 4/2001 | Karpman et al. |
| 6,387,098 B1 | | 5/2002 | Cole et al. |
| 6,582,467 B1 | * | 6/2003 | Teitelbaum et al. ...... 623/17.11 |
| 6,679,890 B2 | | 1/2004 | Margulies et al. |
| 6,692,495 B1 | * | 2/2004 | Zacouto ..................... 606/61 |
| 2001/0021852 A1 | | 9/2001 | Chappius |
| 2002/0138146 A1 | | 9/2002 | Jackson |

(Continued)

FOREIGN PATENT DOCUMENTS

FR 2799638 4/2001

(Continued)

OTHER PUBLICATIONS

Cecil, M. L. et al., "Projection of the S2 Pedicle Onto the Posterolateral Surface of the Ilium—A Technique for Lag Screw Fixation of Sacral Fractures or Sacroiliac Joint Dislocations," Spine 1996, vol. 21, pp. 875-878; www.kalindra.com/project.htm. (6 pages).

(Continued)

*Primary Examiner*—David H. Willse
(74) *Attorney, Agent, or Firm*—Foley & Lardner LLP

(57) ABSTRACT

Systems, bone screws, and methods for delivering a treatment agent into or near a bone, such as a vertebra are provided. The system include a hollow prosthetic vertebral body having one or more fenestrations and a liner containing a treatment agent disposed within the hollow prosthetic vertebral body. The liner is designed to provide for the controlled release of the treatment agent. Also provided are refillable cannulated bone screws having a resealable seal for delivering a treatment agent to a bone.

14 Claims, 2 Drawing Sheets

U.S. PATENT DOCUMENTS

| | | |
|---|---|---|
| 2003/0045885 A1 | 3/2003 | Margulies et al. |
| 2003/0139811 A1* | 7/2003 | Watson et al. ............ 623/11.11 |
| 2003/0212426 A1 | 11/2003 | Olson, Jr. et al. |

FOREIGN PATENT DOCUMENTS

| | | |
|---|---|---|
| WO | WO 02/098307 | 12/2002 |

OTHER PUBLICATIONS

Sato, T. et al., "Calcium Phosphate Augmentation of Screw Fixation in Femoral Neck Fracture," 47th Annual Meeting, Orthopaedic Research Society, Feb. 25-28, 2001, San Francisco, California. (1 page).

Press release from Spine Center Atlanta, "New Screw Debut First-time Use for New Spinal Surgery Device," 2002, Orthopaedic & Spine Surgery of Atlanta LLC; www.SpineCenterAtlanta.com. (2pages).

Instratek Inc., "Titanium Cannulated Bone Screws Minimize Surgery Time by Eliminating Complicated Procedure Steps," www.instratek.com/bone_screw/. (5 pages).

SunMedica—Orthopaedic Surgery Products, "orthoPLUG® Hard Bone Design," Redding, CA 96002; www.xunmedica.com. (one page).

International Search Report mailed on Jun. 1, 2005 for PCT/US04/42636.

* cited by examiner

SYSTEMS AND METHODS FOR AGENT DELIVERY

FIELD OF THE INVENTION

The present invention provides systems and methods for delivering treatment agents to bones, such as vertebra. In particular, the invention provides cannulated, refillable bone screws and prosthetic vertebral bodies designed to provide for the delivery of treatment agents.

BACKGROUND

Degenerative disc disease, spinal trauma and tumors are common and painful conditions suffered by a significant portion of the population. In some instances, the pain and complications caused by these conditions may be bad enough to require that one or more vertebra, facet joints and/or intervertebral discs be removed from the spinal column. In these instances bone fusions, prosthetic discs, prosthetic vertebral bodies, and spinal stabilizing systems, including rods and plates, may be implanted in a patient to alleviate the pain and complications. In addition, disease, trauma and tumors affecting bones, such as vertebra, often require delivery of treatment agents, including therapeutic agents, diagnostic agents and imaging agents to the area of the bone. Unfortunately, the bone implant devices, and in particular the spinal implants, that have been proposed to date do not provide a simple mechanism for combining bone stabilization, repair and/or replacement with treatment agent delivery. Thus, a need exists for devices that combine bone stabilization, repair and/or replacement with treatment agent delivery.

SUMMARY OF THE INVENTION

Systems and methods for delivering one or more treatment agents in or around a spinal column are provided. The systems include a prosthetic vertebral body lined with an internal liner. The prosthetic vertebral body is adapted to replace a natural vertebra and is characterized by an interior surface which defines a hollow internal cavity, an exterior surface and at least one fenestration extending from the interior surface to the exterior surface. The lined internal cavity serves as a reservoir for a treatment agent to be delivered to or near the spinal column. The liner may optionally be biodegradable, such that the agent to be delivered undergoes a controlled release through the liner and the at least one fenestration as the liner degrades. Alternatively, the liner may be permeable to the agent to be delivered to provide a steady controlled release of the agent through the liner and the at least one fenestration.

The liner may be filled or refilled by inserting a syringe through the liner and injecting a treatment agent. The liner is desirably includes a fill port adapted to engage a filling element. For example, the fill port may be covered or stopped with a cap adapted to accept a needle. The fill port may also be adapted to engage with a cannulated bone screw, such that the cannulation in the screw is in fluid communication with the fill port.

Methods for delivering a treatment agent in or near a spinal column include the steps of implanting a vertebral prosthesis in a spinal column, wherein the vertebral prosthesis includes a prosthetic vertebral body lined with an internal biodegradable or permeable liner, and filling the lined cavity with a treatment agent to be delivered. The liner may be filled prior to implantation of the prosthetic vertebral body into a spinal column or after implantation. In addition, the lined cavity is desirably able to be refilled post implantation through a fill port. Refilling may be conducted percutaneously, for example, under fluoroscopic guidance.

Also provided are cannulated bone screws for delivering a treatment agent to a bone or a prosthetic vertebral body. The cannulated bone screws include a shaft portion adapted to be implanted into a bone and a cannulation running through at least a portion of the length of the screw from the screw head. The head of the screw includes a penetrable and resealable seal that permits a filling member to be inserted into the cannulation of the bone screw to fill the cannulation with a treatment agent and that reseals once the filling member has been extracted. In one embodiment, the resealable seal is a cap through with a needle may be inserted. In another embodiment the resealable seal is a one-way valve that opens when an external pressure is applied and reseals when the external pressure is removed. The later embodiment is well-suited for use with an I.V. tube.

DETAILED DESCRIPTION

Figure 1:
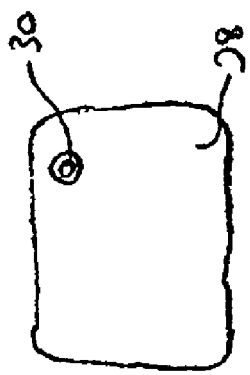
FIG. 1 shows a system for delivering a treatment agent in or near a spine. The system includes a prosthetic vertebral body and a liner.
Figure 1:
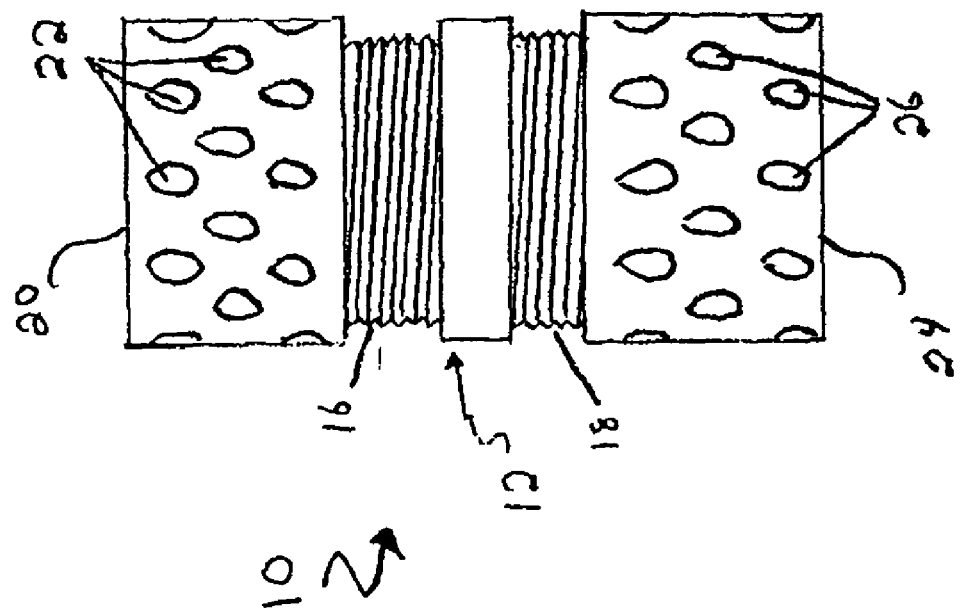

Systems and methods for the internal delivery of a treatment agent to the vicinity of a spinal column are provided. The systems include a prosthetic vertebral body characterized by an interior surface that defines a hollow cavity, an exterior surface and one or more fenestrations extending through the prosthetic vertebral body from the exterior surface to the interior surface. A liner is disposed inside the cavity and covers the one or more fenestrations. The liner may be biodegradable or may be permeable to the treatment agent to be delivered to provide a controlled release of the agent through the liner and the one or more fenestrations to the vicinity of the spinal column.

The prosthetic vertebral body is designed to replace a natural vertebra and may have a variety of shapes and sizes, provided it defines an internal cavity having at least one fenestration. The shape and size of the internal cavity and the number, shape, size and positioning of the fenestrations may vary.

One suitable prosthetic vertebral body that may be used in the systems provided herein is the artificial vertebral body described in U.S. Pat. No. 5,989,290, the disclosure of which is incorporated herein by reference. Briefly, that artificial vertebral body includes a sleeve-shaped central part having a plurality of apertures extending therethrough with oppositely threaded opposing ends. The artificial vertebral body further includes a cylindrical first part having a plurality of apertures extending therethrough screwed onto one end of the sleeve-shaped central part and a cylindrical second part having a plurality of apertures extending therethrough screwed onto the opposing end of the sleeve-shaped central part. When this type of artificial vertebral body is employed, two liners may be used, one disposed in the first cylindrical part and one disposed in the second cylindrical part.

Another prosthetic vertebral body that may be adapted for use in the systems provided herein is described in U.S. patent application Ser. No. 10/675,573, filed Sep. 30, 2003, the disclosure of which is incorporated herein by reference. That prosthetic vertebral body is similar to that disclosed in the '290 Patent, but is adapted to include an artificial disc prosthesis at one or both ends, to provide a prosthetic vertebral assembly that retains at least some of the natural spinal motion provided by the intervertebral discs.

Of course many other prosthetic vertebral body designs are possible. In its simplest form, the artificial vertebral body may be any element having a fenestrated internal cavity that is adapted to be disposed between two vertebrae (real or artificial) in a spinal column, between two intervertebral discs (real or artificial) in a spinal column or between a vertebra (real or artificial) and a intervertebral disc (real or artificial) in a spinal column.

The prosthetic vertebral body may be made of any suitable biocompatible material, many of which are well-known. Examples of suitable biocompatible materials include, but are not limited to, metals such as titanium, titanium alloys, chrome cobalt or stainless steel. Other biocompatible materials include, but are not limited to, graphite and ceramics, such as hydroxyapatites. Plastics may also be employed. Suitable plastics include, but are not limited to, polyethylene (e.g., ultra high molecular weight polyethylene) and polyether ester ketone.

The dimensions (e.g., lateral and anterior-posterior widths and height) of the prosthetic vertebral body are desirably designed to mimic those of a natural vertebra. The prosthetic vertebral body may have a variety of circumferential shapes, including cylindrical or kidney-shapes.

The liner disposed within the hollow cavity of the prosthetic vertebral body may be any film or pouch that covers the one or more fenestrations to prevent the uncontrolled release of a treatment agent. Thus, the liner may be a film partially or wholly covering the interior surface of the cavity or may be a closed pouch that fits within the cavity. The liner is designed to allow for the controlled release of a treatment agent. The controlled release may be a release that is delayed in time or restricted and spread over time. The release may be at a substantially constant rate. In one embodiment, the liner is made from a biodegradable material that degrades in situ after the prosthetic vertebral body has been implanted. In this embodiment, release of a treatment agent contained by the liner is delayed until the liner biodegrades sufficiently. Examples of biodegradable materials from which the liner may be made include, but are not limited to, polylactic acid (PLA) and polyglycolic acid (PGA).

In another embodiment, the liner is made from a material that is permeable to the treatment agent to be released, such that a treatment agent contained by the liner diffuses out of the liner over time. Examples of permeable materials from which the liner may be made include, but are not limited to, biocompatible hydrogels.

In some embodiments the liner is made of a material that is sufficiently porous to be pierced by a needle for filling or refilling the liner. In other embodiments, the liner includes a fill port that is accessible percutaneously such that the lined internal cavity may be filled or refilled percutaneously through a filling member. In one embodiment, the fill port is covered by a cap made of a biocompatible material such as silicone through which a needle may be inserted to fill the lined cavity. In this design, once the needle is removed, the cap reseals to prevent unintended leakage of the treatment agent. Alternatively, the fill port may include a one-way valve designed to accept an inserted filling member, such as a needle, and to reseal after the filling member has been removed.

In another embodiment, the fill port is adapted to engage a cannulated bone screw. In this design the cannulation of the bone screw is in fluid communication with the fill port, such that a treatment agent may be fed into the lined cavity through the bone screw. In this design the bone screw, like the fill port, may include a screw head that is covered by a cap or a one-way valve. The cannulated bone screw may conveniently be part of a stabilizing assembly holding the prosthetic vertebral body in place in a spinal column.

The treatment agent contained within the lined cavity may be any agent that a physician or surgeon deems desirable to deliver to the patient. Examples of the types of treatment agents that may be delivered using the systems provided herein include, but are not limited to, therapeutic agents, diagnostic agents, imaging agents and ablating agents. Specific examples include medications, such as pain killers or chemotherapy agents, antibiotics and bone growth factors.

The systems may be used to deliver a treatment agent to or near a spinal column by implanting a vertebral prosthesis that includes a prosthetic vertebral body having a lined internal cavity, as provided herein, and filling the lined internal cavity with a treatment agent. The lined cavity (e.g., a pouch) may be filled prior to implantation or post implantation and may optionally be refilled post implantation. Filling or refilling may be accomplished using the fill ports and filling members described above. When filling or refilling is done percutaneously, fluoroscopic guidance may be used to position the filling member in the fill port.

FIG. 1 shows an illustrative embodiment of a treatment agent delivery system based on an artificial prosthetic body of the type described in the '290 patent. The system includes an artificial prosthetic body 10 having a sleeve-shaped central part 12 characterized by two opposing oppositely threaded ends 16, 18. A first hollow cylinder 20 having a plurality of fenestrations 22 is screwed onto the first end 16 of the central part 12 and a second hollow cylinder 24 having a plurality of fenestrations 26 is screwed onto the second end 18 of the central part 12. Also shown in the figure is a liner in the form of a closed pouch 28 that may be inserted into one or both of the hollow cylinders. The pouch includes a fill port 30 into which a filling member may be inserted to fill the pouch with a treatment agent.

Cannulated bone screws for delivering a treatment agent to a bone are also provided. The cannulated bone screws include a shaft portion adapted to be implanted into a bone and a cannulation running through at least a portion of the length of the screw from the screw head, and optionally one or more fenestrations along the shaft, extending outwardly from the cannulation. The head of the screw includes a penetrable and resealable seal that permits a filling member to be inserted into the cannulation of the bone screw to fill the cannulation with a treatment agent. The seal reseals itself once the filling member has been extracted. The bone screw may be filled percutaneously, for example, with the help of fluoroscopic guidance. In some embodiments of the invention, the bone screws are implanted for the sole purpose of delivering a treatment agent to a bone or a prosthetic vertebral body. In other embodiments the bone screws are part of a larger spinal implant, such as a fixed or dynamic spinal stabilization system. In this latter embodiment, the bone screws may be used to anchor various parts of a spinal stabilization system, such as a stabilizing plate or rod, a disc prosthesis or a vertebral body prosthesis, in place in and around a spinal column. For example, one of bone screws as provided herein could be used to assemble the spinal stabilization systems described in U.S. patent application Ser.

No. 10/722,119, filed Nov. 25, 2003, the entire disclosure of which is incorporated herein by reference.

In one embodiment, the resealable seal is a cap through with a needle may be inserted. The cap may be made of any material which is biocompatible, soft enough to be pierced by a needle and elastic enough to allow the hole cause by the needle to reseal once the need has been extracted. Silicone is an example of a material from which the cap may be constructed.

In another embodiment the resealable seal is a one-way valve that opens when an external pressure is applied and reseals when the external pressure is removed. For example, the valve may be designed to open when a filling member, such as a needle is pressed against it or when fluid pressure is pressed against it. In the latter embodiment, a tube, such as an I.V. tube may be connected to the head of the screw and a treatment agent may be fed into the cannulation through the I.V.

Figure 2:
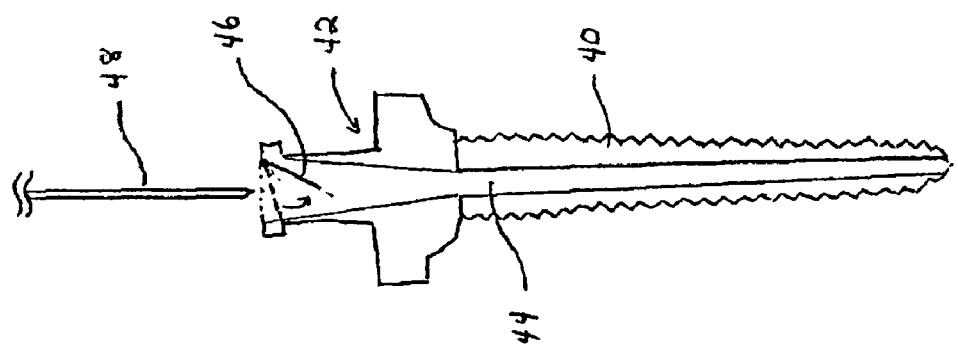
FIG. 2 shows a cross-sectional view of a cannulated bone screw that may be used to deliver a treatment agent to a bone.

FIG. 2 shows a cross-sectional view of an example of a bone screw that may be used to deliver a treatment agent to a bone. The bone screw includes a threaded shaft 40 and a screw head 42. A cannulation 44 extends through the length of the screw. A one-way valve 46 is built into the screw head 42. The valve 46 opens when a filling member (e.g., a needle) 48 is pressed against it and resealed when the filling member is removed.

What is claimed is:

1. A treatment agent delivery system comprising:
   (a) a prosthetic vertebral body designed to replace a natural vertebrae comprising an interior surface defining a hollow cavity, an exterior surface and at least one fenestration extending through the exterior surface and the interior surface;
   (b) a liner disposed within the hollow cavity; and
   (c) a treatment agent disposed within the liner;
   such that the treatment agent may be released from the liner through the at least one fenestration into an intervertebral space when the prosthetic vertebral body is implanted in a spinal column.

2. The system of claim 1, wherein the liner is a pouch.

3. The system of claim 1, wherein the liner comprises a fill port adapted to engage a filling element.

4. The system of claim 3, further comprising a cap covering the fill port.

5. The system of claim 3, further comprising a cannulated bone screw, wherein the cannulation is in fluid communication with the fill port.

6. The system of claim 4, further comprising a needle for refilling the lined cavity through the cap.

7. The system of claim 1, wherein the liner is a biodegradable liner.

8. The system of claim 7, wherein the liner comprises polylactic acid, polyglycolic acid, or a combination thereof.

9. The system of claim 1, wherein the liner is permeable to the treatment agent to be delivered.

10. The system of claim 9, wherein the liner comprises a hydrogel.

11. The system of claim 1, wherein the treatment agent is capable of being injected through a syringe.

12. The system of claim 1, wherein the treatment agent is capable of being fed through a cannulation in a bone screw.

13. A treatment agent delivery system comprising:
   (a) a prosthetic vertebral body comprising an interior surface defining a hollow cavity, an exterior surface and at least one fenestration extending from the exterior surface to the interior surface;
   (b) a liner comprising a fill port, the liner disposed within the hollow cavity; and
   (c) a cannulated bone screw, wherein the cannulation is in fluid communication with the fill port.

14. The treatment agent delivery system of claim 13 further comprising:
   (d) a cap covering the fill port; and
   (e) a needle for refilling the lined cavity inserted through the cap.

* * * * *